United States Patent
Cherkashin et al.

(10) Patent No.: US 10,617,315 B2
(45) Date of Patent: Apr. 14, 2020

(54) DETECTING BIPOTENTIAL WITH AN IONIC VARISTOR

(71) Applicants: Lev Cherkashin, Redmond, WA (US); John Carroll Gordon, Newcastle, WA (US)

(72) Inventors: Lev Cherkashin, Redmond, WA (US); John Carroll Gordon, Newcastle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 761 days.

(21) Appl. No.: 15/282,926

(22) Filed: Sep. 30, 2016

(65) Prior Publication Data

US 2018/0092562 A1    Apr. 5, 2018

(51) Int. Cl.
*A61B 5/0402*   (2006.01)
*G01N 27/04*   (2006.01)
(Continued)

(52) U.S. Cl.
CPC ........ *A61B 5/04026* (2013.01); *A61B 5/0408* (2013.01); *A61B 5/0478* (2013.01);
(Continued)

(58) Field of Classification Search
CPC ..... A61B 5/0006; A61B 5/04; A61B 5/04001; A61B 5/04002; A61B 5/04004;
(Continued)

(56) References Cited

U.S. PATENT DOCUMENTS 5,549,981 A * 8/1996 Maly-Schreiber ...... H01M 2/14
                                                          429/153
6,085,115 A   7/2000 Weaver et al.
(Continued)

OTHER PUBLICATIONS

Galama, et al., "Membrane resistance: The effect of salinity gradients over a cation exchange membrane", In Journal of Membrane Science, Jun. 2, 2014, pp. 279-291.
(Continued)

*Primary Examiner* — Eun Hwa Kim
(74) *Attorney, Agent, or Firm* — Shook, Hardy & Bacon, LLP

(57) ABSTRACT

In various embodiments, methods and systems, of an ionic varistor system is provided. The ionic varistor system includes an electrolyte-membrane assembly having a liquid electrolyte that is enclosed in a solid electrolyte membrane. The ionic varistor system further includes conductive contacts operably coupled to the electrolyte-membrane assembly. The electrolytic-membrane assembly is operably coupled to an electrical potential surface. As the ionic concentration in the electrical potential surface is increased or decreased, some ions diffuse through the solid electrolyte membrane, causing the ions to mix with the liquid electrolyte to achieve an electrostatic equilibrium state that is thermally and mechanically stable. The liquid electrolyte and the diffused ions create an encapsulated ion channel in the electrolyte-membrane assembly. The electrical conductivity of the encapsulated ion channel increases as the ion concentration increases such that the complete electrolyte-membrane assembly produces electrical resistance. The ion concentration is measured as indicator of electrical potential of the electrical potential surface.

20 Claims, 2 Drawing Sheets

(51) Int. Cl.
*G01N 27/327* (2006.01)
*G01N 27/40* (2006.01)
*A61B 5/0408* (2006.01)
*A61B 5/0478* (2006.01)
*A61B 5/0492* (2006.01)
*A61B 5/0496* (2006.01)

(52) U.S. Cl.
CPC .......... *A61B 5/0492* (2013.01); *A61B 5/0496* (2013.01); *G01N 27/04* (2013.01); *G01N 27/327* (2013.01); *G01N 27/40* (2013.01); *A61B 2562/0209* (2013.01)

(58) Field of Classification Search
CPC . A61B 5/0402; A61B 5/0408; A61B 5/04087; A61B 5/0416; A61B 5/042; A61B 5/0421; A61B 5/04284; A61B 5/0476; A61B 5/0478; A61B 5/0488; A61B 5/0496; A61B 5/053; A61B 5/0531; A61B 5/0532; A61B 5/0537; A61B 5/68; A61B 5/6801; A61B 5/6802; A61B 5/6803; A61B 5/6813; A61B 5/6814; A61B 5/6815; A61B 5/6816; A61B 5/6817; A61B 5/6822; A61B 5/6823; A61B 5/6824; A61B 5/6825; A61B 5/6826; A61B 5/6828; A61B 5/6829; A61B 90/90; A61B 2562/0209; A61B 2562/0214; A61B 2562/0215; A61B 2562/0217; G01N 27/50; G01N 27/327; G01N 27/04

See application file for complete search history.

(56) References Cited

U.S. PATENT DOCUMENTS

| | | | |
|---|---|---|---|
| 7,731,827 | B2 | 6/2010 | Astorga-Wells et al. |
| 7,955,326 | B2 * | 6/2011 | Paul .................. A61B 18/1492 606/32 |
| 9,161,707 | B2 | 10/2015 | Hafezi et al. |
| 9,201,058 | B2 | 12/2015 | Hibbs et al. |
| 2002/0177767 | A1 | 11/2002 | Burton et al. |
| 2009/0297905 | A1 | 12/2009 | Fehervari |
| 2015/0276836 | A1 | 10/2015 | Davis et al. |

OTHER PUBLICATIONS

Tobias, et al., "Phospholipid-Cholesterol Membrane Model—Control of resistance by ions or current flow", In Journal of General Physiology, vol. 45, May 1, 1962, pp. 989-1001.

Geise, et al., "Ionic Resistance and Permselectivity Tradeoffs in Anion Exchange Membranes", In Journal of ACS Applied Materials & Interfaces, vol. 5, Issue 10, Sep. 16, 2013, pp. 10294-10301.

"Neuronal Signaling", Published on: May 22, 2001 Available at: http://www.columbia.edu/cu/psychology/courses/1010/mangels/neuro/neurosignaling/neurosignaling.html.

* cited by examiner

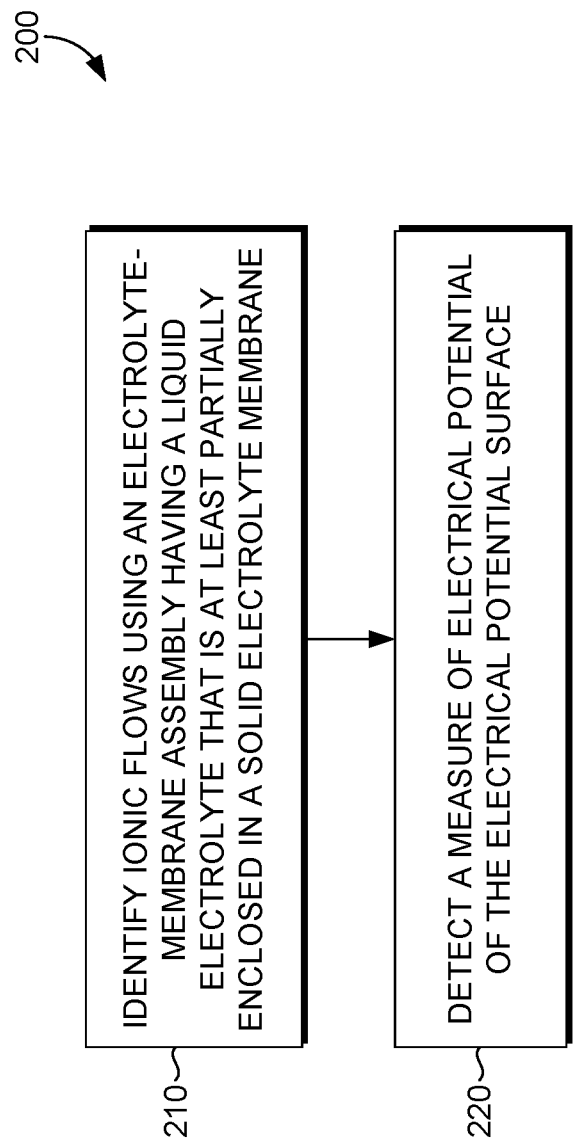

DETECTING BIPOTENTIAL WITH AN IONIC VARISTOR

BACKGROUND

Electrical design refers to grouping of electrical components connected to carry out operations. An electrical system defined by the design can be a portion of a larger electrical system or electronic device. An electrical system or electronic device can include a varistor in the electrical design. A varistor can refer to an electronic component with an electrical resistance. The electrical resistance varies with the applied voltage (e.g., a voltage-dependent resistor—VDR). A varistor includes a nonlinear, non-ohmic current-voltage characteristic for both directions of traversing current. As a result of the operational electrical characteristics of the varistor, the varistor can be a useful component in an electrical design to support controlling and assessing electrical characteristics associated with the electrical design.

SUMMARY

Embodiments described herein provide methods and systems for implementing an ionic varistor system. In particular, the ionic varistor system operates as an electrical interface for assessing electrical potential or biopotential, in particular. The ionic varistor system includes an electrolyte-membrane assembly. The electrolyte-membrane assembly includes a liquid electrolyte that is enclosed in a solid electrolyte membrane. The solid electrolyte has ionomer ionic properties that provide thermal and mechanical stability in the solid electrolyte. The ionic varistor system further includes conductive contacts operably coupled to the electrolyte-membrane assembly. The conductive contacts of the varistor provide an electrical connection with the electrolytic-membrane assembly. The electrolyte-membrane assembly is operably coupled to an electrical potential surface. The ionic concentration of the electrical potential surface can increase or decrease. As the ionic concentration in the electrical potential surface is increased or decreased, some ions diffuse through the membrane, causing the ions to mix with the liquid electrolyte. Mixing the liquid electrolyte with the diffused ions achieves an electrostatic equilibrium state comprising the membrane extending the ionic flows from the electrical potential surface and then in a stable thermal and mechanical state due to the ionomer ionic properties. The liquid electrolyte and the diffused ions create an ion channel in the electrolyte-membrane assembly. The electrical conductivity of the ion channel increases as the ion concentration increases such that the complete electrolyte-membrane assembly produces electrical resistance. The ion concentration is measured as indicator of electrical potential of the electrical potential surface.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

The present invention is described in detail below with reference to the attached drawing figures, wherein;

FIG. 2 is a flow diagram of a method for implementing an ionic varistor system, in accordance with embodiments described herein.

DETAILED DESCRIPTION

Figure 1:
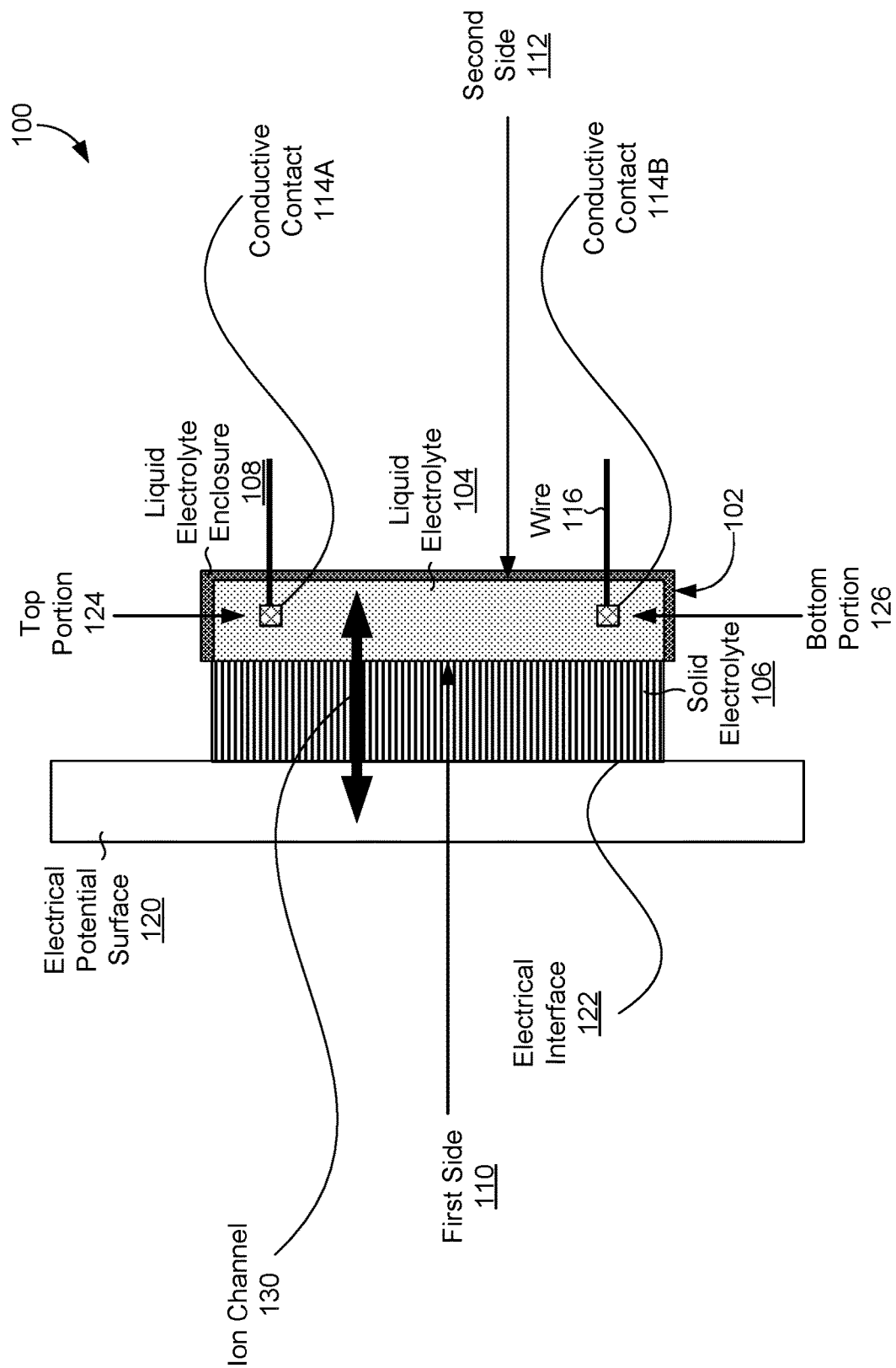
FIG. 1 is a schematic of an exemplary ionic varistor system, in accordance with embodiments described herein.

An electrical system defined by an electrical design can be a portion of a larger electrical system or electronic device. An electrical system or electronic device can include a varistor in the electrical design. A varistor can refer to an electronic component with an electrical resistance. The electrical resistance varies with the applied voltage (e.g., a voltage-dependent resistor—VDR). A varistor includes a nonlinear, non-ohmic current-voltage characteristic for both directions of traversing current. As a result of the operational electrical characteristics of the varistor, the varistor can be a useful component in an electrical design to support controlling and assessing electrical elements in the electrical design.

Embodiments of the present disclosure provide simple and efficient methods and systems for providing an ionic varistor system. By way of example, an ionic varistor can be built using a liquid electrolyte within a solid electrolyte (e.g., fast solid ionic conductor membrane) with metal contacts on either end. The membrane can be advantageously constructed to be a mechanical rigid construction or a thick separator layer that isolates the liquid electrolyte on at least a first side of the membrane. The membrane, when conductive, remains dry due to ionomer ionic properties that extend the ionic flows from an electrical potential surface (e.g., tissue surface or skin) and provide thermal and mechanical stability to the fast solid ionic conductor membrane. A first portion of the surface of the electrolyte-membrane operates as an interface to the skin and a top portion and bottom portion of the membrane include the metal contacts. The metal contacts do not interface with the skin. The metal contacts pierce the membrane and contact the liquid electrolyte within the membrane. The resistance of the liquid electrolyte can change with ion concentration, so the ionic flow would act to control the resistance of the varistor. An external electrical signal (e.g., current or voltage) received via the metal contacts can be used to measure the electrical characteristics in the liquid electrolyte.

Accordingly, with embodiments described herein, an ionic varistor system is provided. The ionic varistor system operates as an electrical interface for assessing electrical potential. The ionic varistor system includes an electrolyte-membrane assembly. The electrolyte-membrane assembly includes a liquid electrolyte that is fully or partially enclosed by a solid electrolyte membrane. The solid electrolyte has ionomer ionic properties that provide thermal and mechanical stability in the solid electrolyte. The ionic varistor system further includes conductive contacts operably coupled to the electrolyte-membrane assembly. The conductive contacts (e.g., metal contacts) of the varistor provide an electrical connection with the electrolytic-membrane assembly. The electrolyte-membrane assembly is operably coupled to an electrical potential surface. The ionic concentration of the electrical potential surface can increase or decrease. As the ionic concentration in the electrical potential surface is increased or decreased, some ions diffuse through the membrane, causing the ions to mix with the liquid electrolyte. Mixing the liquid electrolyte with the diffused ions achieves an electrostatic equilibrium state comprising the membrane extending the ionic flows from the electrical potential surface and a stable thermal and mechanical state due to the ionomer ionic properties.

The liquid electrolyte and the diffused ions create an ion channel in the electrolyte-membrane assembly. The electrical conductivity of the ion channel increases as the ion concentration increases such that the complete electrolyte-membrane assembly produces electrical resistance. The ion concentration is measured as indicator of electrical potential of the electrical potential surface. The electrical resistance may be at least partially inversely proportionate to the ionic concentration in the ion device. An external electrical signal received via the metal contacts can be used to measure the electrical characteristics in the liquid electrolyte. A voltage signal can be transmitted to measure current, or a current signal transmitted to measure voltage. In addition, the ion concentration is measured as indicator of electrical potential of the electrical potential surface based on ionic flows.

In one exemplary electrical system, the ionic varistor system can be part of a biopotential measurement device. In a conventional biopotential measurement device, biopotential measurements can result in low quality measurements because of the elements and processes used in making the measurements. For example, the biopotential measurement device may utilize traditional electrodes that measure voltages resulting from the reduction reaction of a metal in an electrolytic solution. The biopotential measurement device can also use an ion exchange membrane that is water permeable, that operates with mechanical properties, and structurally defined as a thin layer. As the oxidation rate changes, the voltage result from the probe increases or decreases as a result of the changes, and the rate of the reaction is sensitive to ionic concentrations in the electrolyte. The resulting voltages are very low and have to be pushed through amplifiers before the voltages can be measured. Amplifiers generate an inherent noise that makes it difficult to measure potential at high accuracy. Electrical interference, when measurements are based on direct contact with the electrical potential surface, also impacts the accuracy. In addition, the electrodes can be worn out over the term of their use, due the accumulation of oxidized material at the interface, so they have to be replaced fairly often and their signal response profiles vary over the lifetime of use.

Advantageously, ionic varistor system described herein can be used for different types of biopotential measurement techniques. Electrical potential can be expressed as an ionic (not electronic) flow, where the varistors perform high-gain biopotential measurements (e.g., electrocardiogram (ECG), electroencephalogram (EEG), electromyography (EMG) and electro-oculogram (EOG)). The varistor can be operated for extended use without signal quality degradation. Further, ionic varistor system generates a more uniform quality of signal during extended use with limited electrical interference because of the indirect measuring configuration.

With reference to FIG. 1, an exemplary ionic varistor system 100 is illustrated. The ionic varistor system 100 operates as an electrical interface for assessing electrical potential. The ionic varistor system 100 includes an electrolyte-membrane assembly 102. The electrolyte-membrane assembly 102 comprises a liquid electrolyte 104, a solid electrolyte 106, and a liquid electrolyte enclosure 108. In one embodiment, the electrolyte-membrane assembly 102 comprises a solid electrolyte 106 that may fully or partially enclose the liquid electrolyte 104. As depicted, the solid electrolyte 106 partially encloses the liquid electrolyte on a first side 112 (e.g., a solid electrolyte side) and the liquid electrolyte is partially enclosed on a second side 110 (e.g., liquid electrolyte enclosure side) by the liquid electrolyte enclosure 108. It contemplated that the liquid electrolyte enclosure 108 can be made of any suitable material (e.g., plastic or a solid electrolyte). The ionic varistor system 100 further includes one or more conductive contacts (e.g., conductive contact 114A and conductive contact 114B) operably coupled to the electrolyte-membrane assembly. The conductive contacts (e.g., metal contacts) can be located at a top portion 124 and a bottom portion 124, respectively. The conductive contacts of the ionic varistor system 100 provide an electrical connection with the electrolytic-membrane assembly. The electrical connection can be by way of a wire (e.g., wire 116) connected to a corresponding conductive contact. Other arrangements and elements can be used in addition to or instead of those shown, and some elements may be omitted altogether. Further, many of the elements described herein are functional entities that may be implemented as discrete or in conjunction with other components, and in any suitable combination and location.

In operation, the liquid electrolyte 104 shares an electrical interface 122 or makes an electrical contact with the solid electrolyte 106. The solid electrolyte 106 refers to a fast ion conductor having highly mobile ions. By way of example, a solid electrolyte can be Nafion—a sulfonated tetrafluoroethylene based fluoropolymer-copolymer—that supports movement of ions without the need for a liquid or soft membrane. In particular, when the solid electrolyte is conductive based on contact with an electrical potential surface (e.g., electrical potential surface 120), ionic flow associated with the electrical potential surface can be measured. The solid electrolyte 106 has ionomer ionic properties that provide thermal and mechanical stability in the solid electrolyte. Advantageously, the solid electrolyte can be constructed to be mechanically rigid or thick separator layer that isolates the liquid electrolyte 104 on at least the first side 100 of the electrolyte-membrane assembly 102. The electrolyte-membrane assembly 102 is operably coupled to the electrical potential surface 120. The electrical potential surface 120 can be a tissue surface, skin or specifically human skin, where the ionic varistor system 100 is used to measure electrical potential (i.e., biopotential) associated with the skin.

The ionic concentration of the electrical potential surface 120 can increase or decrease. As the ionic concentration in the electrical potential surface increases or decreases some ions diffuse through the membrane, causing the ions to mix with the liquid electrolyte. Mixing the liquid electrolyte 104 with the diffused ions achieves an electrostatic equilibrium state. The electrostatic equilibrium state can include the electrolyte-membrane assembly 102 in a stable thermal and mechanical state due to the ionomer ionic properties. The liquid electrolyte 104 and the diffused ions create an ion channel (e.g., ion channel 130) between the electrical potential surface 120 and the electrolyte-membrane assembly 102. The electrical conductivity of the ion channel increases as the ion concentration increases such that the complete electrolyte-membrane assembly produces electrical resistance. The ion concentration is measured as indicator of electrical potential of the electrical potential surface. The electrolyte-membrane assembly 102, when conductive, remains dry due to ionomer ionic properties that provide thermal and mechanical stability to the solid electrolyte 106.

Turning to FIG. 2, FIG. 2 includes a flow diagram that illustrates a method 200 for detecting electrical potential (e.g., biopotential) using an ionic varistor system. Initially at block 210, ionic flows are identified using an electrolyte-membrane assembly having a liquid electrolyte that is at least partially enclosed in a solid electrolyte membrane. The solid electrolyte has ionomer ionic properties that support extending ionic flows from an electrical potential surface (e.g., skin). The electrolyte-membrane assembly is operably coupled to one or more conductive contacts. Identifying ionic flows can be based on diffused ions from the electrolyte potential surface that create an ion channel with the electrolyte-membrane assembly. The diffused ions mixed with the liquid electrolyte achieve an electrostatic equilibrium state comprising the membrane extending the ionic flows from the electrical potential surface and in a stable thermal and mechanical state due to the ionomer ionic properties. In one embodiment, the electrolyte-membrane assembly is operably coupled to a biopotential measurement device, the biopotential measurement device is one of the following: an electrocardiogram (ECG) an electroencephalogram (EEG); an electromyography (EMG); or an electrooculogram (EOG)).

At block 220, a measure of electrical potential of the electrical potential surface is detected. Detecting the measure of electrical potential of the electrical potential surface is based on transmitting an electrical signal through the one or more conductive contacts operably coupled to the electrolyte-membrane assembly. The solid electrolyte, when conductive, remains dry on at least the electrical interface with the electrical potential based at least in part on the ionomer ionic properties. The ionomer ionic properties provide thermal and mechanical stability in the solid electrolyte.

Embodiments described in the paragraphs below may be combined with one or more of the specifically described alternatives. In particular, an embodiment that is claimed may contain a reference, in the alternative, to more than one other embodiment. The embodiment that is claimed may specify a further limitation of the subject matter claimed.

The subject matter of embodiments of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

A system, as used herein, refers to any device, process, or service or combination thereof. A system may be implemented using components as hardware and special-purpose device, or any combination thereof. A system may be integrated into a single device or it may be distributed over multiple devices. The system may be formed from other systems and components thereof. It should be understood that this and other arrangements described herein are set forth only as examples.

For purposes of this disclosure, the word "including" has the same broad meaning as the word "comprising," and the word "accessing" comprises "receiving," "referencing," or "retrieving." In addition, words such as "a" and "an," unless otherwise indicated to the contrary, include the plural as well as the singular. Thus, for example, the constraint of "a feature" is satisfied where one or more features are present.

Also, the term "or" includes the conjunctive, the disjunctive, and both (a or b thus includes either a or b, as well as a and b).

For purposes of a detailed discussion above, embodiments of the present invention are described with reference to a ionic varistor system; however the ionic varistor system herein is merely exemplary. Components can be configured for performing novel aspects of embodiments, where configured for comprises constructed to perform particular tasks. Further, while embodiments of the present invention may generally refer to a biopotential measurement device and the schematics described herein, it is understood that the techniques described may be extended to other implementation contexts.

Embodiments of the present invention have been described in relation to particular embodiments which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects hereinabove set forth together with other advantages which are obvious and which are inherent to the structure.

It will be understood that certain features and sub-combinations are of utility and may be employed without reference to other features or sub-combinations. This is contemplated by and is within the scope of the claims.

The invention claimed is:

1. An ionic varistor system, comprising:
   an electrolyte-membrane assembly having a liquid electrolyte that is enclosed by a solid electrolyte, the solid electrolyte having ionomer ionic properties that support extending ionic flows from an electrical potential surface; and
   a pair of conductive contacts operably coupled to the electrolyte-membrane assembly to provide an electrical connection between the pair of conductive contacts and the electrolytic-membrane assembly.

2. The system of claim 1, wherein the solid electrolyte is a mechanically rigid fast solid ionic conductor constructed as a separator layer that isolates the liquid electrolyte from an electrical potential surface.

3. The system of claim 1, wherein the solid electrolyte, when conductive, remains dry on at least the electrical interface with the electrical potential based at least in part on the ionomer ionic properties that provide thermal and mechanical stability in the solid electrolyte.

4. The system of claim 1, wherein the solid electrolyte is configured to be operably coupled to an electrical potential surface to extend ionic flows from the electrical potential surface to the electrolyte-membrane assembly, when diffused ions from the electrolyte potential surface create an ion channel with the electrolyte-membrane assembly.

5. The system of claim 1, wherein an ion concentration of the liquid electrolyte is measurable via the pair of conductive contacts as an indicator of an electrical potential of the electrical potential surface.

6. The system of claim 1, wherein the pair of conductive contacts are located at a top portion and a bottom portion, respectively, of the electrolyte-membrane assembly.

7. The system of claim 1, wherein the pair of conductive contacts are operably coupled to corresponding wires, wherein the wires receive electrical signals for measuring electrical characteristics in the liquid electrolyte.

8. The system of claim 1, wherein a conductive contact of the pair of conductive contacts comprises a metal contact operably coupled to the electrolyte-membrane assembly, the metal contact pierces through the electrolyte-membrane assembly contacting the liquid electrolyte.

9. A method for implementing an ionic varistor system, the method comprising:
identifying ionic flows using an electrolyte-membrane assembly having a liquid electrolyte that is at least partially enclosed in a solid electrolyte, the solid electrolyte having ionomer ionic properties that support extending ionic flows from an electrical potential surface, wherein the electrolyte-membrane assembly is operably coupled to one or more conductive contacts; and
detecting a measure of electrical potential of the electrical potential surface.

10. The method of claim 9, wherein identifying ionic flows is based on diffused ions from the electrolyte potential surface that create an ion channel with the electrolyte-membrane assembly.

11. The method of claim 10, where the diffused ions mixed with the liquid electrolyte achieve an electrostatic equilibrium state comprising the membrane extending the ionic flows from the electrical potential surface and in a stable thermal and mechanical state due to the ionomer ionic properties.

12. The method of claim 9, wherein the electrolyte-membrane assembly is operably coupled to a biopotential measurement device, wherein the biopotential measurement device is one of the following:
an electrocardiogram (ECG);
an electroencephalogram (EEG);
an electromyography (EMG); or
an electro-oculogram (EOG).

13. The method of claim 9, wherein detecting the measure of electrical potential of the electrical potential surface is based on transmitting an electrical signal through the one or more conductive contacts operably coupled to the electrolyte-membrane assembly.

14. The method of claim 9, wherein the solid electrolyte, when conductive, remains dry on at least the electrical interface with the electrical potential based at least in part on the ionomer ionic properties that provide thermal and mechanical stability in the solid electrolyte.

15. An ionic varistor system, the system comprising:
an electrolyte-membrane assembly having a liquid electrolyte that is at least partially enclosed by a solid electrolyte, the solid electrolyte having ionomer ionic properties that support extending ionic flows from an electrical potential surface; and
one or more conductive contacts operably coupled to the electrolyte-membrane assembly to provide an electrical connection between the one or more conductive contacts and the electrolytic-membrane assembly.

16. The system of claim 15, wherein the liquid electrolyte is enclosed on a first side by the solid electrolyte and on a second side by a liquid electrolyte enclosure.

17. The system of claim 15, wherein the solid electrolyte is a mechanically rigid fast solid ionic conductor constructed as a separator layer that isolates the liquid electrolyte from an electrical potential surface, wherein the solid electrolyte when conductive remains dry on at least the electrical interface with the electrical potential based at least in part on the ionomer ionic properties that provide thermal and mechanical stability in the solid electrolyte.

18. The system of claim 15, wherein the ionic varistor system is configured for:
identifying ionic flows using the electrolyte-membrane assembly; wherein the electrolyte-membrane assembly is operably coupled to one or more conductive contacts; and
detecting a measure of electrical potential of the electrical potential surface.

19. The system of claim 18, wherein identifying ionic flows is based on diffused ions from the electrical potential surface that create an ion channel with the electrolyte-membrane assembly.

20. The system of claim 19, wherein the diffused ions mixed with the liquid electrolyte achieve an electrostatic equilibrium state comprising a membrane extending the ionic flows from the electrical potential surface and in a stable thermal and mechanical state due to the ionomer ionic properties.

* * * * *